US012558414B2

(12) United States Patent
Dorsey et al.

(10) Patent No.: US 12,558,414 B2
(45) Date of Patent: *Feb. 24, 2026

(54) METHOD FOR VACCINATING AVIANS AGAINST REOVIRUS

(71) Applicant: Biomune Company, Lenexa, KS (US)

(72) Inventors: Kristi Mae Dorsey, Shawnee, KS (US);
Brianna Ford, Lenexa, KS (US);
Christopher Luther, Lenexa, KS (US);
John Knox Rosenberger, Lincoln
University, PA (US)

(73) Assignee: BIOMUNE COMPANY, Lenexa, KS (US)

( * ) Notice: Subject to any disclaimer, the term of this patent is extended or adjusted under 35 U.S.C. 154(b) by 1032 days.

This patent is subject to a terminal disclaimer.

(21) Appl. No.: 17/626,340

(22) PCT Filed: Jul. 13, 2020

(86) PCT No.: PCT/US2020/041793
§ 371 (c)(1),
(2) Date: Jan. 11, 2022

(87) PCT Pub. No.: WO2021/011465
PCT Pub. Date: Jan. 21, 2021

(65) Prior Publication Data
US 2022/0288192 A1     Sep. 15, 2022

Related U.S. Application Data

(60) Provisional application No. 62/873,271, filed on Jul. 12, 2019.

(51) Int. Cl.
| | |
|---|---|
| *A61K 39/21* | (2006.01) |
| *A61K 47/02* | (2006.01) |
| *A61K 47/32* | (2006.01) |
| *A61K 39/00* | (2006.01) |

(52) U.S. Cl.
CPC .............. *A61K 39/21* (2013.01); *A61K 47/02* (2013.01); *A61K 47/32* (2013.01); *A61K 2039/545* (2013.01); *A61K 2039/552* (2013.01); *A61K 2039/55511* (2013.01)

(58) Field of Classification Search
CPC .... A61K 2039/552; A61K 2039/55511; A61K 47/32; A61K 39/12; A61K 47/02; C12N 2720/12034
See application file for complete search history.

(56) References Cited

U.S. PATENT DOCUMENTS 11,813,321 B2 * 11/2023 Dorsey ................. A61K 39/12

FOREIGN PATENT DOCUMENTS

WO      WO 2016/086222      6/2016

OTHER PUBLICATIONS

Written Opinion in International Application No. PCT/US2020/041793, Nov. 3, 2020, pp. 1-8.
Merino-Guzmán, R. et al., American Association of Avian Pathologists—2018 Annual meeting. *American Association of Avian Pathologists*, Jul. 14, 2018, pp. 1-86 (see p. 79), retrieved from the Internet: https://www.aaap.info/assets/2018_Annual_Meeting/AAAP%20Proceedings%20Draft.pdf.
Niu, X. et al. "Preparation and evaluation of goose reovirus inactivated vaccine" *BMC Veterinary Research*, published online Jul. 6, 2017, pp. 1-9, vol. 13, No. 214.
Anonymous, Lohmann Animal Health, "AviPro 431 ND-IB-BD3-REO" *Avian Vaccines*, pp. 1-2, retrieved from the Internet on Jan. 1, 2020: https://www.yumpu.com/en/document/view/35180281/product-information-sheet-for-us-market-only-lohmann-animal-.

* cited by examiner

*Primary Examiner* — Bao Q Li

(74) *Attorney, Agent, or Firm* — SALIWANCHIK, LLOYD & EISENSCHENK

(57)     ABSTRACT

The present invention relates to a method vaccinating avian against reovirus.

17 Claims, No Drawings

METHOD FOR VACCINATING AVIANS AGAINST REOVIRUS

CROSS-REFERENCE TO RELATED APPLICATION

This application claims the benefit of U.S. Provisional Application Ser. No. 62/873,271, filed Jul. 12, 2019.

FIELD OF THE INVENTION

The present invention relates to methods for vaccinating avians against reovirus infection and associated diseases.

BACKGROUND OF THE INVENTION

Avian reovirus (Respiratory Enteric Orphan Virus) are double-stranded RNA viruses that belong to the genus Orthoreovirus from the family Reoviridae. While reovirus infections of poultry are widespread and the majority of avian reovirus cause asymptomatic infections, the pathogenic strains of virus are one of the major causes of economic losses in the poultry industry. The most frequent disease caused by avian reovirus is viral arthritis (tenosynovitis). The main clinical symptom of viral arthritis is swelling of chicken's hock joints causing leg weakness and lameness. Avian reovirus also have been associated with a number of poultry diseases such as myocarditis, hepatitis, malabsorption as well as enteric and respiratory problems. Reovirus infections affect predominantly meat type poultry (broilers) and result in poor growth of affected chickens through their inability to compete for feed with the healthy chickens.

Vaccination is a main control measure used against poultry diseases caused by reovirus. Since chicks are most susceptible to avian reovirus infection, current vaccination approaches usually involve active and passive immunity. Indeed, chicks are most susceptible to avian reovirus infection immediately after hatching and passive immunity, from maternal antibody following vaccination of the breeders, is not always sufficient to efficiently protect chicks against reovirus.

The standard vaccination protocol against reovirus infection comprises to vaccinate chicks during the early days of life (at 7 days of age) with a live attenuated vaccine, such as Nobilis Reo S1133, followed by subsequent vaccination of older chickens (several weeks after the first vaccination), with a live or inactivated vaccine, such as Nobilis Reo inac or Reomune 3. The problems encountered with this protocol are that the use of live attenuated vaccines can lead to safety problems in hatcheries, like inducing the emergence of reovirus variants and inactivated vaccine essentially implies late vaccination programs to avoid adverse reactions in young chickens. Indeed injection of oil emulsion product such as inactivated vaccine may cause post-vaccination reactions. These may include swelling and granulomas at the site of injection (which may cause processing plant condemnations), stiff necks, swollen heads, transient inappetence, and dehydration.

There is currently no vaccination of chicks at one day of age or before 10 weeks of age with an inactivated reovirus vaccine.

There is thus a need for new methods allowing efficient and safe protection of avians against reovirus infection and associated diseases, particularly during early days of life.

SUMMARY OF THE INVENTION

The present invention provides new methods for protecting avians against reovirus infection and associated diseases.

More particularly, the invention provides effective methods for vaccinating avians at very early days of life (e.g., newly-hatched avians) using one or more inactivated reovirus combined with a particular adjuvant system. As shown in the experimental section, such method offers the advantage of allowing efficient and safe protection against reovirus in newly hatched avians, e.g., as early as from day 1 to day 14 of age.

An object of the present invention therefore resides in a method for vaccinating an avian against a reovirus infection or an associated disease, comprising administering to the avian a composition comprising at least one inactivated avian reovirus and an adjuvant comprising a lipophile and a polymer of acrylic or methacrylic acid, wherein the composition is administered to said avian between day 1 and day 14 of age (included).

The invention also provides a method for inducing a protective immune response in an avian against at least one reovirus, comprising administering to the avian between day 1 and day 14 of age a composition as disclosed above.

The invention also provides a method of protecting an avian against a disease or condition resulting from an avian reovirus infection, comprising a step of administering a vaccine as disclosed above to an avian between day 1 and day 14 of age.

In a particular embodiment, the methods of the invention further comprise at least a second administration, preferably at least four weeks after the first administration, typically between 6 to 18 weeks of age. In such prime/boost approach, the boost may be homologous (same as prime) or heterologous (different from prime).

In another aspect, the invention relates to a composition or vaccine comprising at least one inactivated avian reovirus and an adjuvant comprising a lipophile and a polymer of acrylic or methacrylic acid, for use in a method of vaccinating an avian against reovirus infection or a reovirus-associated disease, or in a method of protecting an avian against a disease or condition resulting from an avian reovirus infection, wherein the composition or vaccine is administered to the avian between day 1 and day 14 of age.

In a particular embodiment, the composition or vaccine is administered to the avian between day 1 and day 7 of age.

In a preferred embodiment, the composition or vaccine is administered to the avian within the first 48 hours post hatching, more preferably, within the first 24 hours post hatching.

The invention may be used with any avian. It is particularly suited for poultry, such as chicken and turkeys.

DETAILED DESCRIPTION OF THE INVENTION

The present invention provides new methods for vaccinating avians against reovirus infection. The invention more particularly provides a method allowing efficient and safe vaccination of very young avians, between 1 day to 14 days of age post hatching. The invention is based on the combination of reovirus antigenic material comprising at least one inactivated avian reovirus and a particular adjuvant system which, together, provide efficient and safe vaccination.

The present disclosure will be best understood by reference to the following definitions:

The term "avian reovirus" designates a virus belonging to the species avian Orthoreovirus (R. C. Jones "Avian reovirus infections" Rev. sci. tech. off. Int. Epiz., 2000, 19(2), 614-625).

The term "avian" is intended to encompass all kinds of avians, such as birds of the class of Ayes, i.e., vertebrate animals which are feathered, winged, bipedal, endothermic and egg-laying. In the context of the invention, avians or avian species refer more particularly to birds with economical and/or agronomical interests, such as poultry (such as chickens, turkeys, hens, guinea fowl, quail, partridge and pigeon), waterfowl poultry (such as ducks and geese) and ornamental birds (such as swans, parrot and psittacines).

The terms "antigen" or "antigenic material" designate any substance or agent that when introduced into an organism can stimulate the production of antibodies.

It can be any type of immunogenic material derived from an avian reovirus provided inducing a protective immune response (either by itself or with an adjuvant). The antigenic material may be a "live" attenuated avian reovirus, an inactivated ("killed") avian reovirus, or a part thereof such as a subunit, extract, fraction, recombinant vector, homogenate or sonicate, for instance.

An "immune response" designates the development in a host of a cellular and/or antibody-mediated immune response. Usually, an "immune response" includes the production of antibodies, B cells, helper T cells, and/or cytotoxic T cells, directed specifically to an antigen or antigens of interest. Preferably, the immune response is protective such that resistance to new infection will be enhanced and/or the clinical severity of the disease reduced. For the vaccine according to the invention ("avian reovirus vaccine"), the immune response induced in the vaccinated target animal has for instance the effect of reducing infection by an avian reovirus. This refers to a reduction of the level or the extent of the infection, for example by reducing the viral load or shortening the duration of viral replication in the host animal. This effect is obtained e.g., by preventing or reducing the establishment or the proliferation of a productive infection by avian reovirus in its target organs such as tendon, or intestines. In turn this leads to a reduction in the target animal of the number, the intensity, or the severity of lesions and clinical signs that could be caused by the viral infection. The person skilled in the art is able to determine the effectiveness of a vaccine according to the invention for reducing infection by avian reovirus. For instance, this determination may be done by monitoring the immunological response following vaccination or after a challenge infection, e.g. by monitoring the targets' signs of disease, clinical scores, serological parameters, or by re-isolation of the pathogen, and comparing these results to a vaccination-challenge response seen in mock vaccinated animals. The term "vaccine" as used herein designates a composition which may be used to cause, stimulate or amplify an immune response in an organism, administered for the prevention, amelioration, or treatment of infectious and diseases.

An "adjuvant" is a compound or combination of compounds that enhance, activate, potentiate, or modulate the quality and/or the quantity of the immune response to an antigen.

A "reovirus-associated disease" designates any disease or condition caused by or associated with reovirus infection in an avian. An example of such associated disease is viral arthritis (tenosynovitis), which may comprise swelling of hock joints, leg weakness, and/or lameness. Further diseases associated with reovirus infection include, without limitation, myocarditis, hepatitis, malabsorption, as well as enteric and respiratory problems.

The terms "killed" or "inactivated" can be used interchangeably and refer to an organism (e.g., virus) which has essentially lost the ability to cause disease but retains an immunogenic property thereof, particularly the ability to generate a specific immune response. Inactivated viruses typically are non-infectious or non-virulent, while retaining an immunogenicity, particularly the ability to cause an immune response against a non-inactivated form of the virus. Inactivated viruses may be obtained by various treatments known per se in the art, for instance wherein nucleic acid components have been destroyed by chemical or physical treatment (e.g. formalin, beta-propiolactone, gamma radiation) inducing a suppression in the infectivity of the virus while retaining an antigenicity or immunogenicity of the viral coat.

The term "attenuated reovirus" refers to a live reovirus capable of replication, which is substantially non pathogenic but still able to produce a protective immunity. An attenuated reovirus can for instance contain an attenuating mutation which results in a decreased probability of causing disease in its host (i.e., a loss of virulence) in accordance with standard terminology in the field. A "prime-boost" is a vaccination strategy consisting of administering a vaccine to an animal several times in the aim to protect it against one or several pathogens. The "prime vaccination" named as well "prime vaccine" or "primer" is the first administration of a vaccine composition to an animal inducing an immune response. The "boost vaccination", "boost vaccine" or "booster" is the further administration of a vaccine composition several weeks, months or years after the prime vaccine. The boost vaccine may be administered once or several times depending on the strength and the duration of the immune response induced. The prime and boost vaccines may be vaccine compositions comprising similar (homologous) or different (heterologous) antigenic materials.

The present invention relates to methods for vaccinating avians against reovirus infections and associated diseases. The invention particularly relates to methods for vaccinating young avians, i.e., between day 1 and day 14 of age, thus conferring optimal protection.

In the context of the invention, day 1 (of age) means within 24 hours after hatching. Day 2 of age means between 24-48 hours after hatching. The expression between day 1 and day 14 of age includes from day 1 to day 14, i.e., at any time within 336 hours after hatching.

The method of the invention comprises administering to the avian a composition comprising at least one inactivated avian reovirus and an adjuvant comprising a lipophile and a polymer of acrylic or methacrylic acid. The invention indeed demonstrates such vaccination is sufficient and safe, even when administered very early, e.g., at day 1, day 2, day 3, day 4, day 5, day 6 or day 7 of age. Advantageously, the administration is performed at any time within 144 hours after hatching, preferably at any time within 72 hours after hatching. More preferably, the vaccine is administered to the avian within 48 hours post-hatching, even more preferably within 24 hours post-hatching.

Up to now, efficient avian vaccination against reovirus infections could not be envisioned before at least fourteen (14) days of age, since available vaccines are either inefficient or cause morbidity or mortality in young chicks. The invention surprisingly shows safety and efficacy in young avians, e.g., when used within first 14 days of life, even within first 7 days of life, even within 24 hours post hatching.

It is thus an object of the present invention to provide a method for vaccinating an avian against reovirus infections and associated diseases, comprising administering to an avian between 1 and 14 days of age a vaccine or composition comprising at least one inactivated avian reovirus and an adjuvant comprising a lipophile and a polymer of acrylic or methacrylic acid.

It is also an object of the invention to provide a method (or a vaccine or composition as disclose above for use) for reducing the prevalence of avian reovirus infection in a population or in a geographical area, comprising administering to an avian or a group of avians between 1 and 14 days of age, a vaccine or composition comprising at least one inactivated avian reovirus and an adjuvant comprising a lipophile and a polymer of acrylic or methacrylic acid.

It is also an object of the invention to provide a method (or a vaccine or composition as disclose above for use) for inducing a protective immune response against reovirus infection and associated diseases in avians of 1-14 days of age, comprising administering to said avian a vaccine or composition comprising at least one inactivated avian reovirus and an adjuvant comprising a lipophile and a polymer of acrylic or methacrylic acid.

It is also an object of the invention to provide a method for vaccinating an avian against reovirus infection or an associated disease, comprising a first administration with a composition comprising at least one inactivated avian reovirus and an adjuvant comprising a lipophile and a polymer of acrylic or methacrylic acid, to the avian between day 1 and day 14 of age, and a further administration with a composition comprising at least one avian reovirus antigenic material, to the avian between 6 to 18 weeks of age.

The avian reovirus comprised in the compositions is derived from a similar or a different avian reovirus strain.

The invention uses at least one inactivated avian reovirus. The antigenic material may be derived from any avian reovirus, preferably from a pathogenic or virulent avian reovirus strain. Any serotype may be used. It is particularly suited to use a reovirus field strains isolated from an infected animal, or variants/progeny thereof. Typically, an inactivated virus is a virus which has been structurally altered and is unable to infect a cell. Methods of preparing inactivated viruses are well known per se in the art. Inactivation may be carried out by exposing the virus to a chemical agent such as formaldehyde, paraformaldehyde, b-propiolactone, ethyleneimine, binary ethyleneimine (BEI), or by derivatives thereof. Alternatively, inactivation may be carried out by physical treatments such as heat treatment or sonication. Methods of inactivation are well known to those of skill in the art. The inactivated virus may be concentrated by conventional concentration techniques, in particular by ultrafiltration, and/or purified by conventional purification means, in particular using chromatography techniques including but not limited to gel-filtration, ultracentrifugation on a sucrose gradient, or selective precipitations, in particular in PEG.

For instance, the antigenic material may be derived from an avian reovirus selected from strains S1 (Avian Reovirus 517-14, deposited at ATCC, Patent Depository 10801 University Boulevard, Manassas, Virginia 20110-2209 USA under the terms of the Budapest Treaty, and received the ATCC designation PTA-125155), S2 (Avian Reovirus 516-14, deposited at ATCC, Patent Depository 10801 University Boulevard, Manassas, Virginia 20110-2209 USA under the terms of the Budapest Treaty, and received the ATCC designation PTA-125157), S3 (Avian Reovirus 510-14, deposited at ATCC, Patent Depository 10801 University Boulevard, Manassas, Virginia 20110-2209 USA under the terms of the Budapest Treaty, and received the ATCC designation PTA-125156), S1133, 2408, SS412, 1703, 1733, 1123, 2177, ERS-1 and 3005, or any variant or combination thereof.

In a particular embodiment, the vaccine or composition comprises at least one inactivated avian reovirus, wherein the at least one inactivated avian reovirus is derived from an avian pathogenic reovirus strain.

In another particular embodiment, the vaccine or composition comprises at least two distinct inactivated avian reovirus.

In a particular embodiment, the vaccine or composition comprises at least one avian reovirus selected from strain S1, strain S2 and strain S3, in inactivated form, and an adjuvant comprising a lipophile and a polymer of acrylic or methacrylic acid.

Preferably, the vaccines or compositions contain antigenic material derived from at least two different avian reovirus strains, preferably selected from strain S1, strain S2 and strain S3, in inactivated form.

In a further embodiment, the vaccine or composition comprises an inactivated avian reovirus S1, an inactivated avian reovirus S2 and an inactivated avian reovirus S3, and an adjuvant comprising a lipophile and a polymer of acrylic or methacrylic acid.

In another particular embodiment, the vaccine or composition comprises an inactivated avian reovirus selected from S1133, 2408, SS412, 2177, 1703, 1733, 1123, 2177, ERS-1 and 3005, or any combination thereof, and an adjuvant comprising a lipophile and a polymer of acrylic or methacrylic acid.

In a further particular embodiment, the vaccine or composition comprises an avian reovirus of strain S1133, in inactivated form, and an adjuvant comprising a lipophile and a polymer of acrylic or methacrylic acid.

In a further particular embodiment, the vaccine or composition comprises an avian reovirus of strain SS412, in inactivated form, and an adjuvant comprising a lipophile and a polymer of acrylic or methacrylic acid.

In a further particular embodiment, the vaccine or composition comprises an avian reovirus of strain 2408, in inactivated form, and an adjuvant comprising a lipophile and a polymer of acrylic or methacrylic acid.

In a further particular embodiment, the vaccine or composition comprises avian reovirus of strains S1133 and 2408, in inactivated form, and an adjuvant comprising a lipophile and a polymer of acrylic or methacrylic acid.

In a further particular embodiment, the vaccine or composition comprises avian reovirus of strains S1133, 2408 and SS412, in inactivated form, and an adjuvant comprising a lipophile and a polymer of acrylic or methacrylic acid.

A vaccine or composition used in the invention can also contain or be combined with further antigenic material. Therefore, in an embodiment the composition or vaccine comprises additional antigenic material that is derived from an avian pathogen. This additional antigenic material may derive from another avian reovirus, or from a distinct (different) avian pathogen. Such pathogenic microorganisms are well known in the art. For instance, the avian pathogen may be a virus selected from infectious bronchitis virus, Newcastle disease virus, avian adenovirus, avian astrovirus, avian paramyxovirus, egg drop syndrome virus, fowl adenovirus, infectious bursal disease virus, chicken anaemia virus, avian encephalo-myelitis virus, fowl pox virus, turkey rhinotracheitis virus, duck plague virus, duck viral hepatitis virus, pigeon pox virus, Marek disease virus, avian leucosis virus, infectious laryngotracheitis virus, avian metapneumovirus, avian influenza virus, and goose parvovirus.

As mentioned above, the method combines an inactivated reovirus and a particular adjuvant, which comprises a lipophile and a polymer of acrylic or methacrylic acid.

The lipophile can be any lipophile having medium chain triglycerides. Preferably, the lipophile is selected from the group consisting of medium chain EP triglycerides, medium chain triglycerides NF, medium chain fatty acid triglyceride JPE, caprylic/capric triglyceride, and combinations thereof. The lipophile sold under the name LABRAFAC® (Gattefosse, Lyon, France), which comprises medium-chain triglycerides of caprylic and capric acids, is particularly suited.

The polymer of acrylic or methacrylic acid compound is preferably selected from the polymers of acrylic or methacrylic acid and the copolymers of maleic anhydride and alkenyl derivative. Examples of such compounds include the polymers of acrylic or methacrylic acid which are crosslinked, especially with polyalkenyl ethers of sugars or polyalcohols. These compounds are known by the term carbomer (Phameuropa Vol. 8, No. 2, June 1996). The products sold under the name CARBOPOL® (BF Goodrich, Ohio, USA), comprising carboxypolymethylene and carbomer, are particularly appropriate.

According to the invention, the adjuvant may further comprise at least one compound selected from saline, sterol, preferably cholesterol, alcohol, preferably selected from ethanol, isopropanol, butanol and combination thereof, saponin, preferably Quil A, sodium hydroxide, and any combination thereof. The saline component can be any solution of sodium chloride and water suitable for use in an adjuvant composition.

In a particular embodiment, the adjuvant comprises LABRAFAC™, cholesterol, and Quil-A. In another embodiment, the adjuvant comprises LABRAFAC™, CARBOPOL™, Saline, Cholesterol, Ethanol, Quil-A and Sodium Hydroxide. In a further embodiment, the adjuvant comprises LABRAFAC™, CARBOPOL™ 974P, Saline, vegetable-derived Cholesterol, Ethanol, Quil-A, and Sodium hydroxide. In a particular embodiment, the adjuvant comprises LABRAFAC® Lipophile WL1349 and CARBOPOL® 974P NF Polymer.

The person skilled in the art can also refer to PCT application WO2016/086222, which describes such adjuvant compositions and is thereby incorporated by reference. The products sold under the name VaxLiant ENABL® (AgriLabs, LLC (VaxLiant, LLC)), which comprise a lipophile and a polymer of acrylic and/or methacrylic acid, are particularly appropriate. ENABL P1 is preferably used.

The adjuvant may be added in any suitable amount, such as from about 1 µg to about 10 mg per dose, typically from about 10 µg to about 5 mg per dose, about 750 µg to about 2.5 mg per dose, or in an amount of about 1 mg per dose.

The vaccine according to the present invention may further comprise a suitable solvent, such as for example an aqueous buffer or a phosphate buffer. Preferably, the vaccine also comprises additives. Additives of the present invention may be obtained from any of a number of sources including various proteins and peptides derived from animals (e.g., hormones, cytokines, co-stimulatory factors), and novel nucleic acids derived from viruses and other sources (e.g., double stranded RNA, CpG), and the like which are administered with the vaccine in an amount sufficient to enhance the immune response. In addition, any number of combinations of the aforementioned substances may provide an immunopotentiation effect, and therefore, can form an immunopotentiator of the present invention.

The vaccines of the present invention may further be formulated with one or more further additives to maintain isotonicity, physiological pH and stability, for example, a buffer such as physiological saline (0.85%), phosphate-buffered saline (PBS), citrate buffers, Tris (hydroxymethyl aminomethane (TRIS)), Tris-buffered saline and the like, or an antibiotic, for example, neomycin or streptomycin.

In a particular embodiment, the vaccine or composition can further comprise one or more stabilizers, such as e.g., glycine and/or one or more preservatives, such as e.g., thimerosal. The preservative can notably avoid contamination and/or bacterial growth.

The vaccine may contain a suitable dose to elicit an immune response in the avian, preferably a protective immune response. Optimization of such dose is well known in the art. The amount of antigenic material per dose may be determined by known methods using antigen/anti-body reactions, for example by ELISA. Particularly, the vaccine or composition may comprise from $10^3$ $TCID_{50}$/dose to $10^9$ $TCID_{50}$/dose of at least one antigenic material as described above. Preferably, the titer of antigenic material in the vaccine is from $10^3$ $TCID_{50}$/dose to $10^7$ $TCID_{50}$/dose. In a particular embodiment, the vaccine or composition comprises from $10^3$ $TCID_{50}$/dose to $10^7$ $TCID_{50}$/dose of at least one inactivated avian reovirus.

Advantageously, the antigenic material from each different reovirus strain is preferably present in similar amount.

In a particular embodiment, the vaccine or composition comprises about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of inactivated reovirus S1, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of inactivated reovirus S2, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of inactivated reovirus S3, or derivatives thereof.

In a preferred embodiment, the vaccine or composition comprises between $10^3$ $TCID_{50}$/dose and $10^9$ $TCID_{50}$/dose of each inactivated reovirus strains S1, S2 and S3, or derivatives thereof. In another preferred embodiment, the vaccine or composition comprises between $10^4$ $TCID_{50}$/dose and $10^8$ $TCID_{50}$/dose of each inactivated reovirus strains S1, S2 and S3, or derivatives thereof. In another preferred embodiment, the vaccine or composition comprises between $10^5$ $TCID_{50}$/dose and $10^7$ $TCID_{50}$/dose of each of an inactivated avian reovirus strains S1, S2 and S3, or derivatives thereof.

In a particular embodiment, the vaccine or composition comprises about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of inactivated reovirus S1133, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of inactivated reovirus 2408, and/or about $10^3$ $TCID_{50}$/dose, about $10^4$ $TCID_{50}$/dose, about $10^5$ $TCID_{50}$/dose, about $10^6$ $TCID_{50}$/dose or about $10^7$ $TCID_{50}$/dose of inactivated reovirus 55412, or derivatives thereof. Advantageously, the vaccine is administered at a dose from $10^3$ $TCID_{50}$ to $10^7$ $TCID_{50}$ of antigenic material per avian.

The route of administration can be any route including oral (e.g., gel drop, in feed, in water), ocular (e.g., by eyedrop), oculo-nasal administration using aerosol (e.g., spray), intranasal, cloacal, in ovo, or by injection (e.g., intravenous, subcutaneous, intramuscular, intraorbital, intraocular, intradermal, and/or intraperitoneal) vaccination. The skilled person will easily adapt the formulation of the vaccine composition for each type of route of administration.

Advantageously, the inventors have shown that the combination of the above described adjuvant with inactivated avian reovirus leads to an efficient and safe vaccine, that may be administered by the intramuscular route and/or subcutaneous route.

In a preferred embodiment, the route of administration is intramuscular route, preferably in the thigh or breast muscle.

In another preferred embodiment, the route of administration is subcutaneous (SQ) route. The SQ route is particularly suited for young avians and notably for avians between 1 and 14 days of age.

According to the invention, avians are vaccinated between day 1 and day 14 of age. The invention may be used as a single administration, or with repeated administrations, such as in a prime/boost approach.

The prime vaccination comprises at least one inactivated avian reovirus and an adjuvant comprising a lipophile and a polymer of acrylic or methacrylic acid, administered to the avians between 1 day and 14 days of age.

The boost vaccination may utilize any antigenic material, such as an inactivated reovirus, a live/attenuated reovirus, or any other antigenic material derived therefrom. Preferably however, the method uses a homologous prime-boost, wherein the same vaccine composition is used for both priming and boosting.

In such a prime-boost vaccination, the boost is preferably administered to the avians between 6 and 18 weeks of age, preferably between 10 and 15 weeks of age, for instance at 12 weeks of age.

The preferred time span between prime and boost is between 6 and 18 weeks.

A preferred vaccination regimen is a prime vaccination administered between 1 and 14 days of age, and a boost vaccine about 6-18 weeks after the prime.

It is thus an object of the present invention to provide a vaccine comprising one or more inactivated reovirus strains and an adjuvant comprising a lipophile and a polymer of acrylic or methacrylic acid for use for vaccinating an avian against at least one reovirus, wherein the vaccine is administered to said avian between day 1 and day 14 of age, and optionally again between 6 and 18 weeks of age.

The dose and route of administration used in the prime/boost approach is the same as exposed above.

In a preferred embodiment, the route of administration for the vaccination of avians between 1 and 14 days of age is preferably a subcutaneous (SQ) route of administration, and the route of administration for the vaccination of avians, between 6 and 18 weeks of age, is preferably an intramuscularly route of administration.

Further aspects and advantages of the invention will be disclosed in the following experimental section, which is illustrative of the claimed invention.

Examples

1. Safety and Efficacy Studies of Inactivated Trivalent and Monovalent Reovirus Vaccines as Prime Vaccines

1.1. Material

The avian virus strains S1, S2 and S3 respectively deposited on PTA-125155; PTA-125157 and PTA-125156 under the terms of the Budapest Treaty with the ATCC, and S1133 were used.

Inactivated reoviruses were prepared by chemical inactivation with formaldehyde solution.

The adjuvant ENABL® P1, which comprises a lipophile and a polymer of acrylic and/or methacrylic acid, is manufactured by AgriLabs, LLC (VaxLiant, LLC) and is purchased in a ready-to-use form. The tested vaccine included the ENABL® P1 adjuvant at a 10-20% (v/v) final concentration.

Vaccines: A monovalent inactivated reovirus vaccine comprising inactivated S1133 and ENABL was prepared, for a total antigen titer of between $10^5$ and $10^7$ $TCID_{50}$ per 0.5 mL dose. The reovirus, glycine, and thimerosal solutions were mixed until homogenous prior to the addition of the adjuvant, ENABL® P1 (Vaxliant). The final solution was mixed until homogenous prior to aliquoting into bottles.

A trivalent vaccine comprising inactivated avian reovirus strains S1, S2, and S3 combined with VaxLiant ENABL® P1 adjuvant was prepared containing between $10^5$ and $10^7$ $TCID_{50}$ of each respective strain for a total antigen titer of between $10^5$ and $10^7$ $TCID_{50}$ per 0.5 mL dose. The antigens were produced on chicken cells. Each of the antigens was concentrated following inactivation. The reovirus antigens, glycine, and thimerosal solutions were mixed until homogenous prior to the addition of the adjuvant, ENABL® P1 (Vaxliant). The final solution was mixed until homogenous prior to aliquoting into bottles.

The formulation of the trivalent vaccine is provided in Table 1.

TABLE 1

| Formulation of the trivalent vaccine | | | |
|---|---|---|---|
| Component | Designation | ATCC designation | Final Quantity Per 0.5 mL |
| Reovirus S1 | 517-14 | PTA-125155 | $10^5$ to $10^7$ $TCID_{50}$[1,2] |
| Reovirus S2 | 516-14 | PTA-125157 | $10^5$ to $10^7$ $TCID_{50}$ |
| Reovirus S3 | 510-14 | PTA-125156 | $10^5$ to $10^7$ $TCID_{50}$ |
| VaxLiant ® ENABL ® P1 | N/A[3] | N/A | 10-20% v/v |
| Glycine Solution | N/A | N/A | 0-80%[4] |
| Thimerosal Solution | N/A | N/A | ≤1:10,000 |

[1]$TCID_{50}$/mL = 50% tissue culture infectious dose per milliliter

[2]A final titer containing $10^5$ and $10^7$ $TCID_{50}$ per dose for each respective strain (S1, S2 and S3) was in serial vaccine composition.

[3]NA = not applicable

[4]Volume of glycine solution dependent on amount of antigen to reach required viral titer per dose.

Placebo: The same adjuvant, ENABL® P1, was used in the product-matched placebo and the antigen components were substituted with extra glycine solution.

1.2 Protocol

This study was randomized, double-blind, controlled trials. Fertile eggs were collected from SPF chickens from the same source (Valo, flock RF6-19) and these embryos were hatched at the same time and housed in the same room for the duration of the study.

Method of Vaccination

Prime vaccination: At 1 day of age, 91 healthy chicks were randomly divided into four treatment groups. One respective vaccine preparation comprising a total antigen titer of between $10^5$ to $10^7$ $TCID_{50}$ per 0.5 mL dose.

For IM vaccination, each chicken from group A, B and C received a dose of 0.5 mL of either monovalent vaccine, trivalent vaccine or placebo administered intramuscularly at 12 weeks of age.

Method of Challenge

Challenge Organism: The challenge organism was avian reovirus strain S1 in virulent form. The challenge total antigen titer is $10^{2.5}$ $TCID_{50}$ per 0.1 mL. The reovirus strain S1 used in this study is the most pathogenic of the three strains used in the trivalent vaccine.

Chickens of treatment groups A, B and C were challenged by footpad injection at 4 weeks post boost vaccination with 0.1 mL of virulent strain S1 (challenge dose: $10^{2.5}$ $TCID_{50}$/ dose). The group D did not receive challenge dose but a placebo which is not composed of ENABL.

The methods of vaccination and challenge are provided in Table 2.

TABLE 2

| | | | | | |
|---|---|---|---|---|---|
| | | | | Methods of vaccination and challenge | |
| Group ID | Number of animals in the trial | $1^{st}$ Vaccine 1DOA[2] - Route and quantity | $2^{nd}$ Vaccine 12WOA[3] - Route and Dose | Number of animals at time of challenge | Challenge $10^{2.5}$ $TCID_{50}$/0.1 mL |
| A: monovalent vaccine | 27 | SQ - 0.2 mL | IM-0.5 mL | 22 | 0.1 mL Footpad |
| B: trivalent inactivated vaccine | 27 | SQ - 0.2 mL[4] | IM[6] - 0.5 mL | 23 | injection at 4 weeks post |
| C: Placebo | 27 | SQ - 0.2 mL | 0.2 mL | 23 | vaccination |
| D: Negative control - Not vaccinated | 10 | N/A[1] | N/A | 10 | Not challenged |

[1]N/A = not applicable

[2]DOA = day of age

[3]WOA = week of age

[4]A final titer containing $10^5$ and $10^7$ $TCID_{50}$ per dose for each respective strain (1, 2, 3) and S1133 was in serials vaccine composition. For prime vaccination, 0.2 mL of the vaccine was administered to each chicken. Thus, there was a total antigen titer between $10^5$ and $10^7$ $TCID_{50}$ per dose.

[5]SQ = subcutaneous route of administration

[6]IM = intramuscular route of administration treatment group (group A) composed of 27 healthy chickens was vaccinated via the subcutaneous (SQ) route with the monovalent inactivated vaccine. A second treatment group (group B) composed of 27 healthy chickens was vaccinated via the SQ route with the trivalent inactivated vaccine. A third treatment group (group C) comprising 27 healthy chickens were vaccinated with product-matched placebo (Placebo). A fourth treatment group (group D) composed of 10 healthy chickens was not vaccinated (negative control).

Boost vaccination: At 12 weeks of age, each group A, B and C was respectively vaccinated via intramuscular (IM) route with monovalent vaccine, trivalent vaccine or product-matched placebo. The group D did not receive a challenge dose.

For SQ vaccination, each chicken from group A, B and C received a dose of 0.2 mL of either monovalent vaccine, trivalent vaccine or placebo administered subcutaneously at 1 day of age. The dose of 0.2 mL has been collected from the

2.1 Results 2.1.1. Safety Results

Chickens were observed daily for mortality and adverse events.

There were no mortalities attributable to vaccination. At 7 days of age, 4 chickens from each treatment groups A, B and C have been randomly chosen in order to observe the injection site of reaction (ISR). Only 2 on the 12 chickens receiving ENABL adjuvant with or without antigen presented lesions, which lesions were mild (mild swelling and/or discoloration of the inoculated side). The two chickens with lesions had each a total score of 3 from a max lesion score of 32. The 10 other chickens observed do not have lesions (Table 3).

Inactivated reovirus vaccines formulated with an adjuvant comprising a lipophile and a polymer of acrylic or methacrylic acid (ENABL® P1) thus appear to be safe in very early day of age of chickens.

TABLE 3

| | | | Number of animal for ISR[1] observation at 7 DOA[2] | | |
|---|---|---|---|---|---|
| Group ID | Number of animals per treatment group | Vaccination 1DOA - Administration Route and Dose | | Lesions observed | Lesions score (max = 32) |
| A: monovalent vaccine | 27 | SQ[5] - 0.2 mL | 4 | 1 | 3 |
| B: trivalent inactivated vaccine | 27 | SQ - 0.2 mL[4] | 4 | 1 | 3 |
| C: Placebo | 27 | SQ - 0.2 mL | 4 | 0 | N/A[3] |
| D: Negative control - Not vaccinated | 10 | N/A | N/A | N/A | N/A |

[1]ISR = injection site of reaction
[2]DOA = day of age
[3] N/A = not applicable
[4]A final titer containing $10^5$ and $10^7$ TCID$_{50}$ per dose for each respective strain (1, 2, 3) and S1133 was in serials vaccine composition. For vaccination, 0.2 mL of the vaccine was administered to each chicken. Thus, there was a total antigen titer between $10^5$ and $10^7$ TCID$_{50}$ per dose.

2.1.2 Efficacy Results

Severity Categorization

Severity of footpad lesions was determined by examining the right footpad of each bird on each day of the 14 day observation period. A score between zero (0) to three (3) was assigned to each footpad. The scoring system is an adaptation of the scoring system used to score reovirus injected footpads in a published study (Wu et. al, 2005). In addition, swelling observed on days 1 and 2 was disregarded as transient swelling due to the inoculation event. A score of zero (0) was assigned when there was no sign of inflammation. A score of one (1) was assigned when there was mild swelling of the inoculated side. A score of two (2) was assigned when there was severe swelling and/or discoloration of the inoculated side. A score of three (3) was assigned when there was severe swelling and signs of viremic spread up the inoculated leg and/or into the non-inoculated footpad. A footpad was protected from reovirus challenge associated lesions if it did not display severe swelling; thus, if the footpad did not receive a score of two (2) or higher for 2 or more consecutive days from 3-14 days post-challenge, it was considered protected from Reovirus S1 challenge strain respectively.

Protection Against Reovirus Strain S1

The reovirus challenge model used in this study is the most pathogenic of the three strains used in the trivalent vaccine. Efficacy is summarized in the following Table 4.

TABLE 4

Efficacy Summary

| Group ID | Challenge Dose | % chickens infected | Number of chickens infected/Total | Prevented Fraction |
|---|---|---|---|---|
| D: Negative Control | Placebo (without adjuvant) | 0% | 0/10 | N/A |
| C: Placebo | $10^{2.5}$ | 100% | 23/23 | N/A |
| B: Trivalent vaccine | TCID$_{50}$/dose | 17% | 4/23 | 83% |

15

16

The results show the method of vaccination is effective and prevented severe lesions.

Good results were also obtained for the monovalent vaccine, showing its efficacy in preventing reovirus infection.

CONCLUSIONS

The safety and efficacy studies on an inactivated avian reovirus vaccine formulated with an adjuvant comprising a lipophile and a polymer of acrylic or methacrylic acid indicate that the method for vaccinating an avian is safe, effective and prevents severe lesions against reovirus infection when administered in very early day of age of chickens.

What is claimed is:

1. A method for vaccinating an avian against a reovirus or an associated disease, comprising administering to the avian a composition comprising at least one inactivated avian reovirus and an adjuvant comprising a lipophile and a polymer of acrylic or methacrylic acid, wherein the composition is administered to the avian between day 1 and day 14 of age.

2. The method of claim 1, wherein the composition is administered to the avian between day 1 and day 7 of age.

3. The method of claim 2, wherein the composition is administered to the avian within 24 hours post-hatching.

4. The method of claim 1, wherein the composition comprises at least two distinct inactivated avian reoviruses.

5. The method of claim 1, wherein the at least one inactivated avian reovirus is an avian pathogenic reovirus strain.

6. The method of claim 1, wherein the inactivated reovirus is selected from inactivated strains S1, S2, S3, S1133, 2408, SS412, 2177, 1703, 1733, 1123, ERS-1 and 3005.

7. The method of claim 1, wherein the composition comprises inactivated reovirus strains S1, S2 and S3.

8. The method of claim 1, wherein the composition is administered at a dose from $10^3$ $TCID_{50}$ to $10^9$ $TCID_{50}$ of antigenic material per avian.

9. The method of claim 1, wherein the lipophile is selected from the group consisting of medium chain EP triglycerides, medium chain triglycerides NF, medium chain fatty acid triglyceride JPE, caprylic/capric triglyceride, and combinations thereof.

10. The method of claim 1, wherein the adjuvant further comprises at least one compound selected from saline, sterol, alcohol, saponin, sodium hydroxide, and any combination thereof.

11. The method of claim 1, wherein the avian is a poultry.

12. The method of claim 1, wherein a further administration with a composition comprising at least one avian reovirus antigenic material administered to the avian between 6 to 18 weeks of age.

13. The method of claim 12, wherein the avian reovirus in the compositions is derived from a similar or a different avian reovirus strain.

14. A method for inducing a protective immune response in an avian against at least one reovirus, comprising administering to said avian a vaccine comprising at least one antigenic material comprising at least one inactivated avian reovirus and an adjuvant comprising a lipophile and a polymer of acrylic or methacrylic acid, wherein the vaccine is administered to the avian between day 1 and day 14 of age.

15. The method of claim 11, wherein the poultry is a chicken.

16. The method of claim 10, wherein the sterol is cholesterol.

17. The method of claim 10, wherein the alcohol is selected from ethanol, isopropanol, butanol and combinations thereof.

* * * * *